US010589062B2

(12) United States Patent
Zhang et al.

(10) Patent No.: US 10,589,062 B2
(45) Date of Patent: Mar. 17, 2020

(54) ADJUSTABLE CURVED MEDICAL CATHETER AND ASSEMBLING METHOD THEREOF

(71) Applicant: Lifetech Scientific (Shenzhen) Co., Ltd., Shenzhen (CN)

(72) Inventors: Tingchao Zhang, Shenzhen (CN); Yang Li, Shenzhen (CN); Quanjie Jiang, Shenzhen (CN); Mingyang Cai, Shenzhen (CN)

(73) Assignee: Lifetech Scientific (Shenzhen) Co. Ltd., Shenzhen (CN)

( * ) Notice: Subject to any disclaimer, the term of this patent is extended or adjusted under 35 U.S.C. 154(b) by 301 days.

(21) Appl. No.: 15/317,889

(22) PCT Filed: Jun. 9, 2015

(86) PCT No.: PCT/CN2015/081090
§ 371 (c)(1),
(2) Date: Dec. 9, 2016

(87) PCT Pub. No.: WO2015/188740
PCT Pub. Date: Dec. 17, 2015

(65) Prior Publication Data
US 2017/0113017 A1    Apr. 27, 2017

(30) Foreign Application Priority Data

Jun. 13, 2014    (CN) .......................... 2014 1 0265996

(51) Int. Cl.
*A61M 25/01*    (2006.01)
*A61M 25/00*    (2006.01)

(52) U.S. Cl.
CPC ........ *A61M 25/0043* (2013.01); *A61M 25/01* (2013.01); *A61M 25/0136* (2013.01);
(Continued)

(58) Field of Classification Search
CPC .......... A61M 25/0043; A61M 25/0133; A61M 25/0136; A61M 25/0147; A61M 2025/0163
See application file for complete search history.

(56) References Cited

U.S. PATENT DOCUMENTS

| | | | | |
|---|---|---|---|---|
| 4,740,195 A | * | 4/1988 | Lanciano | A61M 25/0017 600/434 |
| 5,807,331 A | * | 9/1998 | den Heijer | A61M 25/0021 600/585 |

(Continued)

FOREIGN PATENT DOCUMENTS

| CN | 102580225 A | 7/2012 |
|---|---|---|
| CN | 204016479 U | 12/2014 |

OTHER PUBLICATIONS

First office action in corresponding China application No. 201410265996.9.
(Continued)

*Primary Examiner* — Nathan R Price
*Assistant Examiner* — Courtney B Fredrickson
(74) *Attorney, Agent, or Firm* — Raymond Sun

(57) ABSTRACT

An adjustable curved medical device includes a catheter, a handle, and a traction wire provided in the catheter. The distal end of the traction wire is connected to the distal end of the catheter. A retainer device is provided in the handle, and includes a rotating member and a body having a receiving groove for receiving the rotating member, and a guiding hole extending through the outer wall of the body to the receiving groove. A slot formed between the rotating member and the inner wall of the body is smaller than the diameter of the traction wire. The proximal end of the traction wire extends through the guiding hole and engages in the slot.

20 Claims, 6 Drawing Sheets

(52) U.S. Cl.
CPC .. *A61M 25/0147* (2013.01); *A61M 2025/0163* (2013.01); *A61M 2207/00* (2013.01)

(56) References Cited

U.S. PATENT DOCUMENTS

| | | | | |
|---|---|---|---|---|
| 9,161,759 B2* | 10/2015 | Lee | ............... | A61B 17/12022 |
| 2005/0256452 A1* | 11/2005 | DeMarchi | ......... | A61M 25/0017 |
| | | | | 604/95.04 |
| 2011/0054446 A1* | 3/2011 | Schultz | ............... | A61B 5/04 |
| | | | | 604/528 |
| 2014/0336573 A1* | 11/2014 | Yu | ............... | A61M 25/0136 |
| | | | | 604/95.04 |

OTHER PUBLICATIONS

Second office action in corresponding China application No. 201410265996.9.

\* cited by examiner

ADJUSTABLE CURVED MEDICAL CATHETER AND ASSEMBLING METHOD THEREOF

TECHNICAL FIELD

The present invention relates to a medical device, and in particular, relates to an adjustable curved medical catheter and assembling method thereof.

PRIOR ART

A medical catheter is a medical device widely applied to minimally-invasive interventional diagnosis and surgery. Compared with the conventional medical catheters, the adjustable curved medical catheter has an adjustable curved distal end, which is capable of reaching the target lesion position rapidly and reliably to reduce the surgery time. The adjustable curved medical catheter comprises but is not limited to an adjustable curved electrophysiological catheter and an adjustable curved sheath. The adjustable curved sheath is used for establishing a passage in the human body to deliver or retrieve an implant, deliver drugs, or export body fluid. The electrophysiological catheter is inserted into a human blood vessel through percutaneous puncture under the monitoring of an X-ray angiography machine for guiding the electrode tip to the target position in the blood vessel, and intra-cardiac sensing, recording, stimulating and temporary pacing during arrhythmia evaluation.

The adjustable curved medical catheter generally comprises a catheter, a traction mechanism and a handle. The distal end of the catheter may be curved unidirectionally or multidirectionally in a desired direction, or restored to the straight configuration by pulling the traction wire. As a result, the catheter is delivered smoothly and flexibly in the curved and multi-branched vessels of human body to the target site. In the field of interventional medical instruments, typically, the end which is closer to an operator is referred to as a proximal end, and the other end which is farther is referred to as the distal end.

In related art, the traction wire is generally fixed in the handle by means of steel tube pressing or welding so that the sheath can be adjusted to be curved by pulling the traction wire. However, the traction wire must be treated whether fixed by steel tube pressing or welding. For example, the traction wire will be flattened if fixed by steel tube pressing. On the other hand, if fixed by welding, the physical strength at the welding site of a traction wire will be less than a half of that compared with a non-welded one. The material strength may be greatly reduced due to the stress concentration of the welding point, the changing of the cross-sectional dimension, surface morphology and residual stress or other factors according to the metal welding theory. Therefore, all the above treatment methods change the inherent profile and material property of the traction wires, reduce the connection strength and reliability of traction wires, and thus reduce the reliability of the curve adjustment.

Furthermore, the treatment methods in the related art are very complicated. For example, in the steel tube pressing process, the magnitude of the pressing force during the steel tube pressing process has a great influence on the connection strength; that is, the connection reliability is very sensitive to the magnitude of the pressing force. This type of design requires high standards for processing. If the pressing force is excessive, the surface of the traction wire may be damaged which will reduce the tensile strength. If the pressing force is insufficient, the steel tube will not have enough deformation, which leads to a low friction force between the steel tube and the traction wire, low connection reliability, a higher risk of being pulled out, and curve adjustment failure. In the welding process, the welding process is difficult to implement due to the slender traction wire. Furthermore, the welding process has high requirements for equipments and complicated process parameters because of the narrow welding area. In particular, it is difficult to control the welding point position during the welding process, and the qualification rate of the process is very low.

SUMMARY OF THE INVENTION

A technical problem to be solved by the invention is to provide an adjustable curved medical catheter and assembling method thereof, which has the advantages of a solid and reliable connection, high reliability of curve adjustment and high flexibility, a simple fabrication process, and low cost for eliminating the shortcomings in the prior art, such as low connection strength of the retainer device, complicated and unreliable process formation, and high possibility of product dysfunction.

To achieve the objects of the present invention, there is provided an adjustable curved medical catheter which comprises a catheter, a handle, and a traction wire disposed in the catheter. The distal end of the traction wire is connected to the elastic distal end of the catheter. The adjustable curved medical catheter further comprises a retainer device disposed in and connected to the handle. The retainer device comprises a body and a rotating member. The body has a receiving groove and a guiding hole extending from the outer wall of the body to the receiving groove. The rotating member is received in the receiving groove. A slot formed between the rotating member and the inner wall of the body is smaller than a height of the traction wire. The proximal end of the traction wire passes through the guiding hole and engaged in the slot.

In the adjustable curved medical catheter, the outer wall of the rotating member is provided with a groove, and the sum of the groove depth and the slot width is lightly smaller than the diameter of the traction wire, and the proximal end of the traction wire sandwiched between the groove and slot.

In the adjustable curved medical catheter, the rotating member is provided with a through hole extending through the guiding hole, and the proximal end of the traction wire further passes through the through hole.

In the adjustable curved medical catheter, at least one of the outer wall of the rotating member and the inner wall of the body is elastically deformed under the winding and squeezing of the traction wire.

In the adjustable curved medical catheter, the rotating member and the body are respectively provided with a stop mechanism cooperating with each other to fix the position of the rotating member after rotation.

In the adjustable curved medical catheter, the body is provided with at least three guiding holes, and the proximal end of the traction wire passes through one of the guiding holes and turns back to pass through the remaining guiding holes.

In the adjustable curved medical catheter, at least one of the outer wall of the rotating member and the inner wall of the body is provided with an anti-slip member.

In the adjustable curved medical catheter, the rotating member and the receiving groove are both polygonal structures cooperating with each other.

The invention also provides an assembling method of the adjustable curved medical catheter, comprising steps as following:

extending the proximal end of the traction wire through the guiding hole provided on the body of the retainer device;

rotating the rotating member which causes the traction wire to be wound around the outer wall of the rotating member until the traction wire is engaged between the rotating member and the receiving groove of the body for housing the rotating member.

The assembly method of the adjustable curved medical catheter further comprises a step of dropping fixing glue into the slot after the traction wire is engaged in the slot.

In the adjustable curved medical catheter of the present invention, the retainer device can adjust the curve of the catheter distal end by adjusting the traction wire, and the reliability of the curve adjustment property of the catheter is determined by the connection between the retainer device and the traction wire. In order to avoid a failure during curve adjustment due to unreliable connection caused by the steel tube pressing and welding process in the prior art. the present invention fixes the traction wire by adopting the engaging connection, that is to say, a tight fit is formed by an engagement between the retainer device body the rotating member and the traction wire which is implemented for fixing the traction wire. Because the gap (or the slot) between the rotating member and the inner wall of the receiving groove is a slightly smaller than the diameter of the traction wire, the rotating member wound around by the traction wire engages with the inner wall of the receiving groove to form the tight fit; as a result, the proximal end of the traction wire is retained in the slot formed between the rotating member and the retainer device, thereby fixing the proximal end of the traction wire on the retainer device. Because a large static friction force is generated between the receiving groove and the rotating member due to the traction wire engaging between the inner wall of the receiving groove and the rotating member, and the static friction is greater than the reaction generated by the curved distal end of the catheter, the fixing is very firm and reliable which prevents the traction wire from being pulled out. Meanwhile, this type of connection does not require any treatment on the traction wire or any other exterior processing treatments (such as welding or pressing), so that the material property of the traction wire will not change. Therefore, the connection between the traction wire and the rotating member has high tensile strength and fatigue resistance, and the reliability of the connection is greatly improved when compared with the prior art. As a result, the reliability of curve adjustment is improved, and there is no need to change the material property.

According to the assembly method of the adjustable curved medical catheter of the present invention, the fixing of the traction wire may be implemented simply by rotating the rotating member to retain the traction wire in the slot. The retainer device can fix the traction wire without any exterior processing treatments (such as welding or pressing), and the process is simple and does not require additional devices or complex processing procedures, thereby reducing the personnel training and device maintenance costs.

DESCRIPTION OF THE DRAWINGS

The invention will be further described with reference to the accompanying drawings and examples, in the drawings.

DETAILED DESCRIPTION OF THE INVENTION

Figure 1:
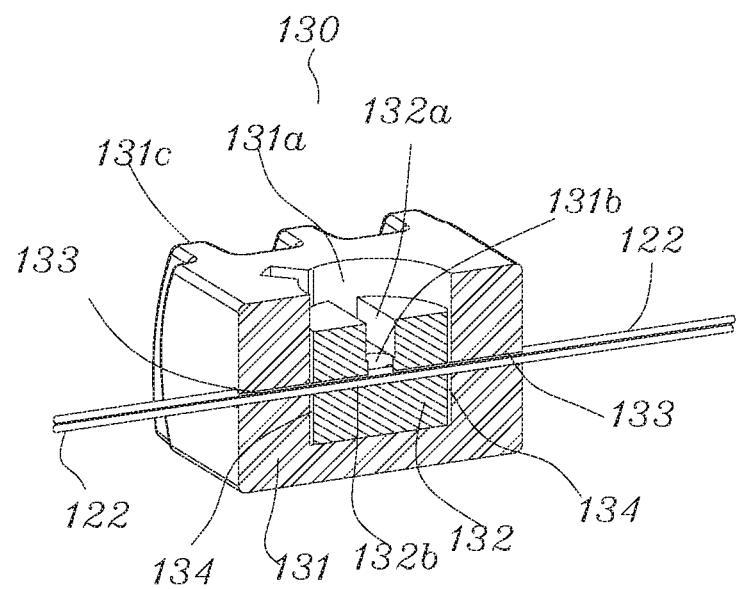
FIG. 1 is a schematic view of a retainer device according to the present invention.

In order to understand the technical features, objects and effects of the invention more clearly, the embodiments of the invention will be now described in detail with reference to the drawings.

As shown in FIGS. 1-17, an adjustable curved medical catheter comprises a catheter 110, a handle 140, and a traction wire 122 disposed in the catheter 110. The distal end of the traction wire 122 is connected to the elastic distal end of the catheter 110. The adjustable curved medical catheter further comprises a retainer device 130 disposed in the handle 140 and connected to the handle 140 which comprises a body 131 and a rotating member 132. The body 131 has a receiving groove 131a and a guiding hole 133 extending through the outer wall of the body 131 to the receiving groove 131a. The rotating member 132 is received in the receiving groove 131a. A slot 134 having a diameter less than that of the traction wire 122 is formed between the rotating member 132 and the inner wall of the body 131. The proximal end of the traction wire 122 passes through the guiding hole and is retained in the slot 134.

FIG. 1 illustrates the structure of the retainer device 130. Rotating teeth 131c are formed on the outside of the body 131 and slide along the inner tooth groove in the rotating drum of the handle 140. The receiving groove 131a is preferably disposed in a direction perpendicular or inclined to the moving direction of the retainer device 130. The rotating member 132 received in the receiving groove 131a is capable of rotating relative to the receiving groove 131a. In an exemplary embodiment, the rotating member 132 has a rotary adjustment member 132a for rotating the rotating member 132. The body 131 has a guiding hole 133 for allowing the traction wire 122 to extend through the outer wall of the body 131 to the receiving groove 131a. The rotating member 132 has a through hole 132b extending through the rotating member 132 for allowing the traction wire 122 to pass through. The slot 134 formed between the rotating member 132 and the diameter of the receiving groove 131a is slightly smaller than that of the traction wire 122 which allows the traction wire 122 to extrude the rotating member 132 and the receiving groove 131a when being wound on the outer wall of the rotating member 132 for retaining the relative position between the rotating member 132 and the receiving groove 131a.

Figure 2:
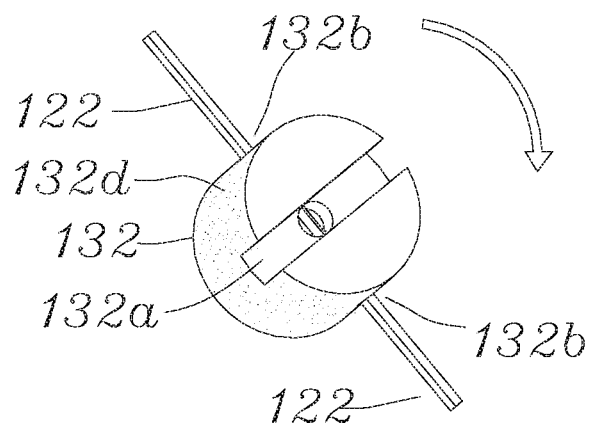
FIG. 2 is a schematic view of a rotating member in a static state according to the present invention.
Figure 3:
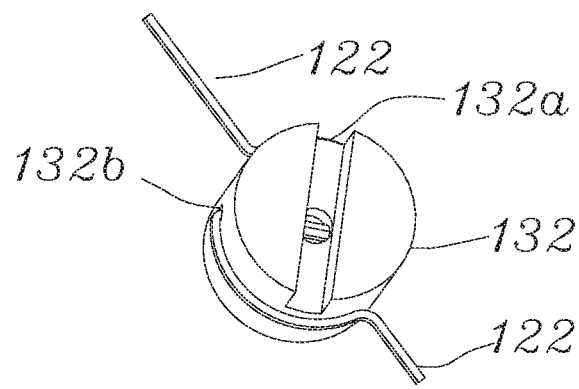
FIG. 3 is a schematic view of the rotating member after rotating according to the present invention.

As shown in FIGS. 1-3, the body 131 is the primary structure of the entire retainer device 130. Since the retainer device 130 is disposed in the rotating drum, the shape of the body 131 should not be limited as long as it is slidable in the rotating drum. In general, the body 131 is column-shaped, preferably cylindrical. In the embodiment shown in the drawings, the rotating teeth 131c extend from the outer wall of the body 131 in a manner that the structure, size and pitch of the rotating teeth 131c cooperate with the rotating drum. Because of the receiving groove 131a, the rotating teeth 131c are in discontinuous arrangement; for example, it is at least not provided in the position of the receiving groove 131a. In this example, a part of the body 131 is cut along the pulling direction of the traction wire 122 to form a platform, the receiving groove 131a is located on the platform, and another platform is formed opposite to the platform where the receiving groove 131a is located, so that the body 131 is flat and both sides of the retainer device 130 have an arc shape to allow the cylindrical structure to fit inside the rotating drum.

As one of the functions of the retainer device 130 is to adjust the pulling of the traction wire 122 along the moving direction of the retainer device 130, the moving direction of the retainer device 130 is the axial stretching direction of the traction wire 122. When rotating the rotating drum, the rotating teeth 131c of the body 131 slide in an axial direction of the rotating drum under the action of the tooth groove in the rotating drum. The retainer device 130 pulls the traction wire 122 to move along an axial direction. The receiving groove 131a being perpendicular or oblique to the moving direction of the retainer device 130 means that the extending direction of the receiving groove 131a is not parallel to the pulling and moving directions of the traction wire 122; only in this way can the rotating member 132 be placed in the receiving groove 131a to cooperate with the receiving groove 131a to fix the traction wire 122. Preferably, the extending direction of the receiving groove 131a is perpendicular to the moving direction of the retainer device 130. The depth of the receiving groove 131a should fit the height of the rotating member 132. Further, considering the stability, the depth of the receiving groove 131a is generally at least half of the height of the body 131. However, the difference between the height of the body 131 and the bottom of the receiving groove needs to meet the strength requirements. Considering the need for the rotating member 132 to rotate relative to the receiving groove 131a, the receiving groove 131a is cylindrically shape, which may also be modified, or alternatively added with other parts.

Another key function of the rotating member 132 is to fix the traction wire 122. In order to achieve this function, a guiding hole 133 is formed on the body 131 and a through hole 132b is formed on the rotating member 132. Both of the holes 133 and 132b are through holes. The guiding hole 133 extends through the outer wall of the body 131 to the receiving groove 131a and the through hole 132b extends through the entire rotating member 132. The relative position of the guiding hole 133 and the through hole 132b is preferably as follows: when the rotating member 132 is disposed in the receiving groove 131a, the guiding hole 133 and the through hole 132b correspond to each other. Thus, the traction wire 122 passes through the guiding hole 133 and the through hole 132b in sequence.

As shown in FIGS. 1-3, in order to achieve the fixing function, the width of the slot 134 between the receiving groove 131a of the body 131 and the rotating member 132 should be slightly smaller than the diameter of the traction wire 122. As shown in FIG. 3, when the rotating member 132 is rotating in the receiving groove 131a, the traction wire 122 winds around the outer wall of the rotating member 132 for passing through the guiding hole 133 and the through hole 132b. As shown in FIG. 1, since the width of the slot 134 between the receiving groove 131a and the rotating member 132 is slightly smaller than the diameter of the traction wire 122, a squeezing force is generated by the traction wire 122 wound on the outer wall of the rotating member 132 and the inner wall of the receiving groove 131a to form an interference fit. Consequently, the width of the slot 134 between the receiving groove 131a and the rotating member 132 is decided by the material of the outer wall of the rotating member 132 and the inner wall for forming the receiving groove 131a, and the structure and the shape of both the rotating member 132 and the inner wall of the receiving groove 131a.

Since both the rotating member 132 and the inner wall for forming the receiving groove 131a are made of hard materials, the deformations of the rotating member 132 and the inner wall for forming the receiving groove 131a are very small, the slot 134 formed therebetween needs to be carefully adjusted to meet the requirements of pressing and fixing the traction wire 122, and also the adjustment of the rotating member 132. The traction wire 122 is made of metals or polymers, preferably a metal wire. For example, the traction wire 122 may be a metal wire having a round or flat shape and having a diameter of about 0.05-0.25 mm. Specifically, the metal wire may be a stainless steel wire, a tungsten alloy wire, a cobalt-chromium alloy wire, or a nickel-titanium alloy wire, etc. As the traction wire 122 is preferably a stiff metal wire, at least one of the outer wall of the rotating member 132 and the inner wall of the receiving groove is elastically deformed for easy operation under the pressure due to the winding of the traction wire 122. As elastomers may have a larger deformation and also generate a larger friction force, the winding and the fixing may be more efficient and reliable. Since at least one of the outer wall of the rotating member 132 and the inner wall of the receiving groove 131a must be capable of elastically deforming, the contact portion between the rotating member 132 and the receiving groove 131a is elastic. Alternatively, at least one of the rotating member 132 and the body 131 is an entire elastomer. Preferably, the rotating member 132 is an elastomer. The specified material of elastomers is selected according to the actual needs for fixing and rotating. For example, plastics and rubber materials may be selected.

After the rotating member 132 stops rotating and the traction wire 122 is adjusted to the effective length, the traction wire 122 is fixed by the pressure between the rotating member 132 and the receiving groove 131a. In order to improve the fixing stability of the traction wire 122, the traction wire 122 may be wound multiple times around the rotating member 132, which is capable of making the fixing more reliable, because the traction wire 122 has a longer contacting area along the axial direction with both the inner wall of the receiving groove 131a and the outer wall of the rotating member 132, which causes a higher static friction between the traction wire 122 and the receiving groove 131a and between the traction wire 122 and the rotating member 132. This static friction is much higher than the reaction applied to the traction wire 122 in the axial direction generated by the curved distal end of the catheter. Therefore, the fixing method is very stable and reliable, and is capable of avoiding the problem of haring the traction wire 122 pulled off. The number of wound turns of the traction wire 122 around the rotating member 132 depends on the actual pulling force on the traction wire 122.

During above assembling process, the length of the proximal end of the traction wire located in the slot is adjusted by rotating the rotating member. In contrast, in the prior art, once the traction wire is fixed, the length of the traction wire cannot be adjusted again during operation, and the adjustment property of the catheter cannot be controlled according to actual needs. Therefore, when compared with the prior art, the present invention can further adjust the length of the traction wire wound into the slot for a plurality of times to change the effective working length of the traction wire, thereby fitting individual use circumstances.

As shown in FIG. 2, for improving the connection stability between the traction wire 122 and the rotating member 132 and the connection stability between the traction wire 122 and the receiving groove 131a, the inner wall of the receiving groove 131a and/or the outer wall of the rotating member 132 can further be provided with an anti-slip member 132d to increase the friction between the traction wire 122 and the rotating member 132 in the receiving groove 131a and prevent relative sliding therebetween. The anti-slip member 132d can preferably be a friction surface provided on at least one surface between the outer wall surface of the rotating member 132 and the inner wall surface of the receiving groove 131a. The friction surface refers to a surface obtained by a process to create roughness to the surface for increasing the friction. The anti-slip member 132d can further be a protrusion or a groove provided on the inner wall of the receiving groove 131a or the outer wall of the rotating member 132 to increase the friction between the traction wire 122 and the outer wall of the rotating member 132, and between the traction wire 122 and the inner wall of the receiving groove 131a, thereby improving the connection stability. Alternatively, after the effective length of the traction wire 122 is determined, a glue is injected into the slot 134 which solidifies as the anti-slip member 132d for fixing the rotating member 132 in the receiving groove 131a, preventing relative movement therebetween, and preventing the rotating member 132 from rotating under the pulling force of the traction wire 122.

As shown in FIG. 1, the rotating member 132 is placed in the receiving groove 131a of the body 131. To prevent the rotating member 132 from separating from the receiving groove 131a, the rotating member 132 can be rotatably connected in the receiving groove 131a. The rotating connection is carried out in such a way that a limiting post 131b extends along the axial direction of the receiving groove 131a, and the rotating member 132 surrounds the limiting post 131b so that radial movement is limited by the limiting post 131b which only allows the rotating member 132 to rotate.

Figure 16:
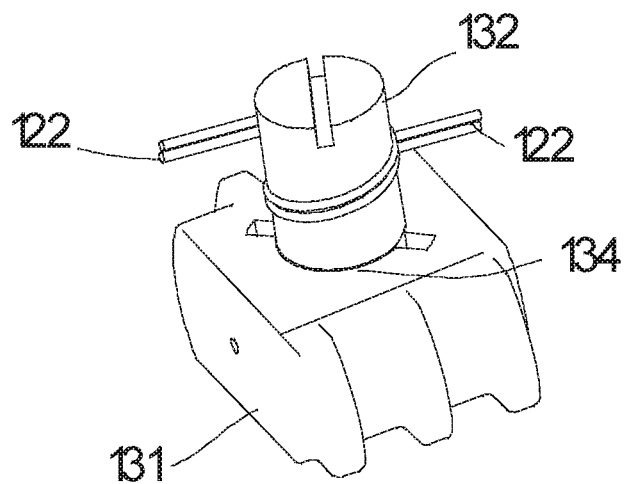
FIG. 16 is an assembled view of the rotating member having a groove assembled with a receiving groove according to the present invention.
Figure 17:
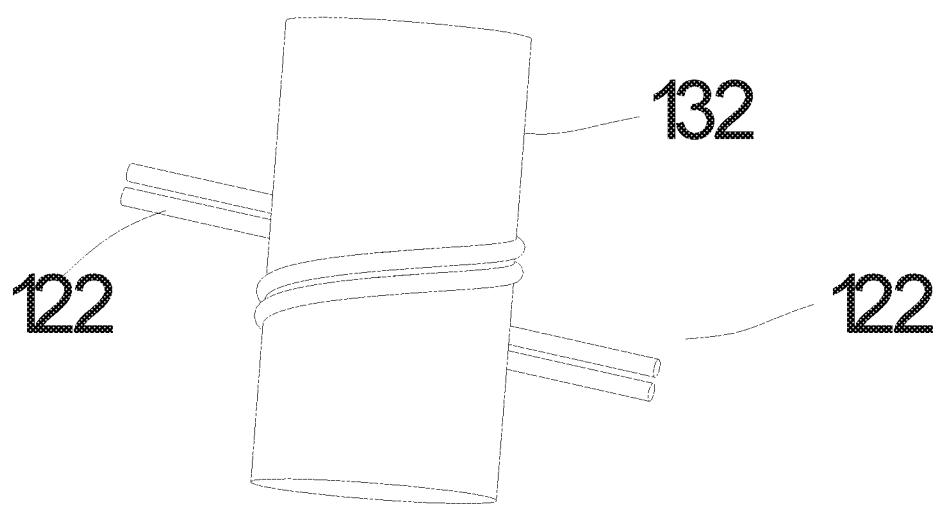
FIG. 17 is an assembled view of the rotating member having a groove assembled with the traction wire according to the present invention.

Another preferred embodiment of connecting the rotating member and the receiving groove according to the present invention is shown in FIGS. 16 and 17. The difference from the above embodiment is that the rotating member 132 in this preferred embodiment is provided with a groove, and the sum of the depth thereof and the width of the slot 134 is slightly smaller than the diameter of the traction wire. During the assembling process, after the proximal end of the traction wire 122 passes through the guiding hole 133, the traction wire 122 rotates with the rotating member 132 and is wound thereon. When the rotating member 132 is housed in the receiving groove 131a, the traction wire 122 is retained in the space enclosed by the groove and the slot 134. The groove is helically wound around the outer wall of the rotating member 132, and the traction wire 122 is correspondingly wound into the groove. The space formed by the groove and the slot 134 is smaller than the diameter of the traction wire 122. This configuration further provides a tight fit among the traction wire 122, the rotating member 132 and the receiving groove 131a, and locks the traction wire 122 and the rotating member 132 in the receiving groove 131a.

Between the guiding hole 133 provided in the body 131 and the through hole 132b provided in the rotating member 132, the guiding hole 133 is only used for the traction wire 122 to pass therethrough. The position of the guiding hole 133 corresponds to the position of the traction wire 122 in the catheter for which the traction wire 122 can be smoothly stretched. The guiding hole 133 is preferably provided in the center position of the body 131 which can avoid the contact friction between the traction wire 122 and the inner wall of a rotating drum. The shape of the guiding hole 133 should not be limited. It can be any shape that allows the traction wire 122 to pass therethrough. For the traction wire 122 to pass smoothly through the body 131, the guiding hole 133 is designed as a straight hole, though the guiding hole 133 can alternatively be a curved hole and other non-straight hole which is capable of increasing the friction between the traction wire 122 and the wall of the guiding hole 133, and thereby increasing the stability of the fixing.

The body 131 can have one or two, and even three or more guiding holes 133. The proximal end of the traction wire 122 alternately passes through the remaining guiding holes 133 after passing through a pair of the guiding hole 133. When one guiding hole 133 is provided, the terminal end of the traction wire 122 is rotated and wound on the rotating member 132. When two guiding holes 133 are provided, the traction wire 122 penetrates the receiving groove 131a from one guiding hole 133 and extends out of the receiving groove 131a from the other guiding hole 133, or the traction wire 122 penetrates the receiving groove 131a from one guiding hole 133 and subsequently penetrates the through hole 132b on the rotating member 132, finally extending out of the receiving groove 131a from the other guiding hole 133. In general, the traction wire 122 passes through the body 131. The two guiding holes 133 can be provided in pairs and stretched in a straight line, or not. Preferably, a pair of guiding holes 133 is provided on both sides of the receiving groove 131a, respectively, and in the same straight line.

Figure 4:
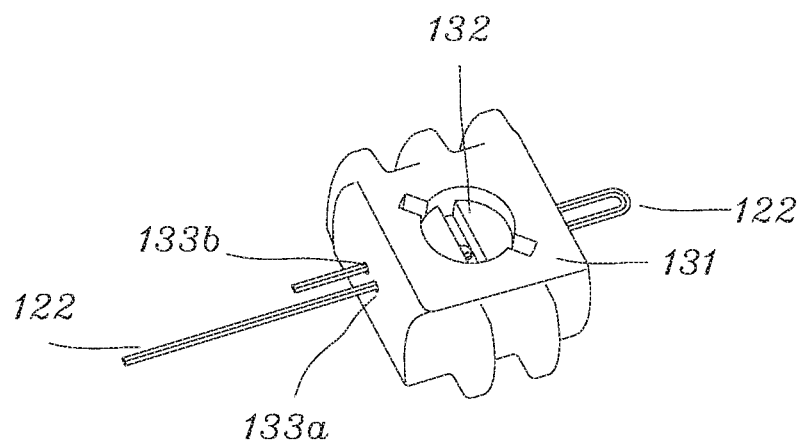
FIG. 4 is a schematic view of a rotating member provided with a plurality of guiding holes according to the present invention.

As shown in FIG. 4, when at least three guiding holes 133 are provided, the traction wire 122 can pass through a first guiding hole 133a and a second guiding hole 133b in pairs of all the guiding holes 133. The first guiding hole 133a is provided in the center for ensuring that the force and the displacement can be transmitted coaxially. The second guiding hole 133b is provided on one side of the first guiding hole 133a. When passing through the first guiding hole 133a, the traction wire 122 turns back and passes through the second guiding hole 133b. After turning back over and over, it would be difficult to pull the traction wire 122 from the retainer device 130, and simultaneously double passes of the traction wires 122 are sandwiched between the rotating member 132 and the body 131, which increases the friction between the rotating member 132 and the body 131, and prevents the rotating member 132 from rotating back. The rotating member 132 can be further provided with a plurality of through holes corresponding to the plurality of guiding holes, and the traction wire 122 extends through one of the through holes while extending through the guiding hole, and then turns back to extend through other through holes.

As shown in FIGS. 1-10, because friction exists between the rotating member 132 and the receiving groove 131a, and in order to meet a need for a larger external force loaded on the rotating member 132, a rotary adjustment member 132a for driving the rotating member 132 is provided on the rotating member 132. The rotating adjustment member 132a is provided on the top surface of the rotating member 132 to rotate the rotating member 132 conveniently through the opening of the receiving groove 131a. The rotary adjustment member 132a has a variety of configurations. One example is an adjusting groove that is formed on the top surface of the rotary adjustment member 132a, and operating by a tool corresponding with the adjusting groove in shape and driving the rotating member 132 to rotate. Specifically, the tool extends into the adjusting groove with a shape at its front end that matches the shape of the adjusting groove and a clearance formed therebetween, so that the front end of the tool engages the inner wall of the adjusting groove in the rotating direction and drives the rotating member 132 rotate. The adjusting groove can be provided in many shapes, such as a slotted groove, a cross groove and a polygonal groove. The rotary adjustment member 132a can also be a protrusion provided on the top surface of the rotating member 132 for being rotated by hand or a tool clamping the protrusion. The rotating adjustment member 132a can comprise an adjusting groove and an adjusting rod formed in the top surface of the rotating member 132. One end of the adjusting rod rotatably connects with one end of the adjusting groove, and before rotation, a free end of the adjusting rod is pulled up and the adjusting rod is rotated by tool or by hand to drive the rotating member 132 to rotate. FIGS. 1 to 3 show rotation by the adjusting groove, the rotating member 132 being rotated by a screwdriver extended into the adjusting groove 132a. For example, by rotating the rotating member 132 in the arrow direction shown in FIG. 2, the rotation of the rotating member 132 will drive the traction wire 122 passing through the guiding hole 133 to curve with the rotation of the rotating member 132 and to wind around the outer wall of the rotating member 132 and be disposed in the slot 134.

Furthermore, for locking the adjusted rotating member 132, the rotating member 132 and the receiving groove 131a are respectively provided with a stop mechanism 136 for fixing the rotated rotating member in a certain position. The stop mechanism 136 can be provided on the wall surfaces of the rotating member 132 and the receiving groove 131a, or provided directly on the top surfaces of the rotating member 132 and the body 131. Thu, the rotating member 132 can be locked not only by the friction existing among the wall of the receiving groove 131a, the rotating member 132 and the traction wire 122, but also by adding the stop mechanism 136.

Figure 5:
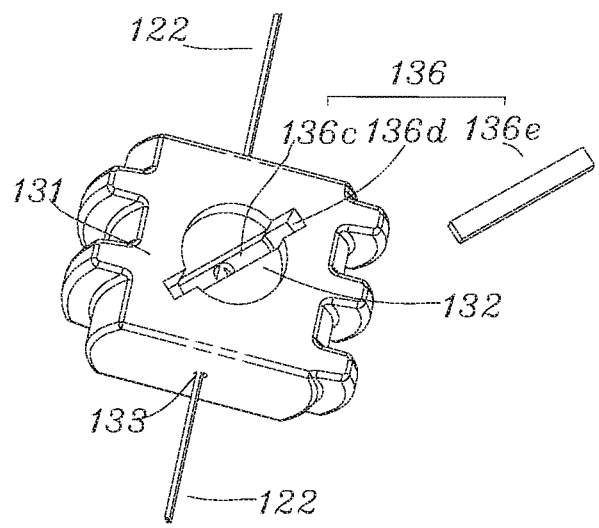
FIG. 5 is a schematic view of a stop mechanism according to a first embodiment in the present invention.
Figure 6:
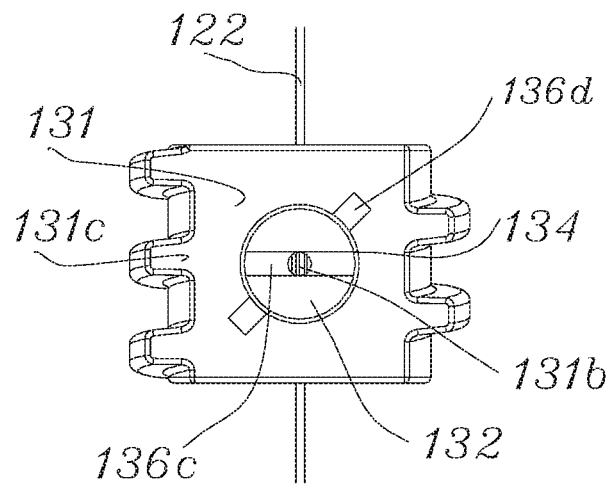
FIG. 6 is a schematic view of the stop mechanism according to the first embodiment in a static state in the present invention.
Figure 7:
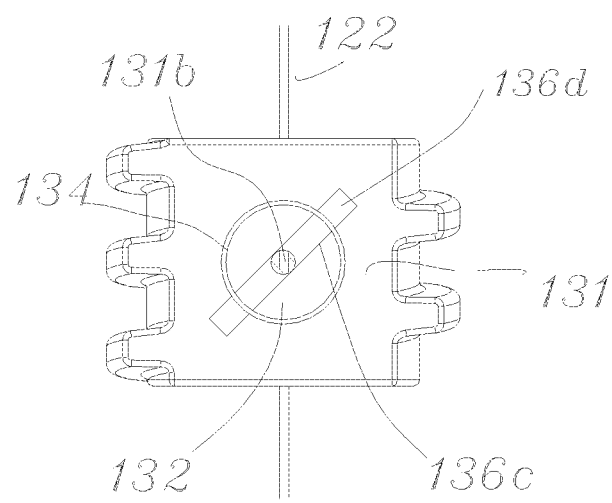
FIG. 7 is a schematic view of the stop mechanism according to the first embodiment after rotating in the present invention.

The stop mechanism 136 can be embodied in various embodiments, and the first embodiment is shown in FIGS. 5 to 7. The stop mechanism 136 comprises a stop groove and a stop block 136c. Specifically, a first stop groove 136c is formed in the top surface of the rotating member 132, at least one second stop groove 136d is formed in the top surface of the body 131, and the first stop groove 136c is a through groove having at least one through side. When the rotating member 132 is not rotating, the relative position between the second stop groove 136d and the first stop groove 136c is illustrated in FIG. 6. As shown in FIG. 7, when the rotating member 132 is rotated to a certain angle, the first stop groove 136c and the second stop groove 136d align to form one complete groove. When a stop block 136e is placed in the first stop groove 136c and the second stop groove 136d, the position of the rotating member 132 is locked. The relative position between the first stop groove 136c and the second stop groove 136d is decided by the desired effective length of the traction wire 122 which is specifically set according to the actual requirements. Furthermore, the shapes and configuration of the first stop groove 136c and the second stop groove 136d are not limited as long as they can be aligned at a certain rotating angle. In this embodiment, the first stop groove 136c and the second stop groove 136d are linear grooves, so correspondingly the stop block 136e is also linear-shaped. The number of the second stop grooves 136d is designed according to the actual requirements, and preferably the number is 1 to 3.

Figure 8:
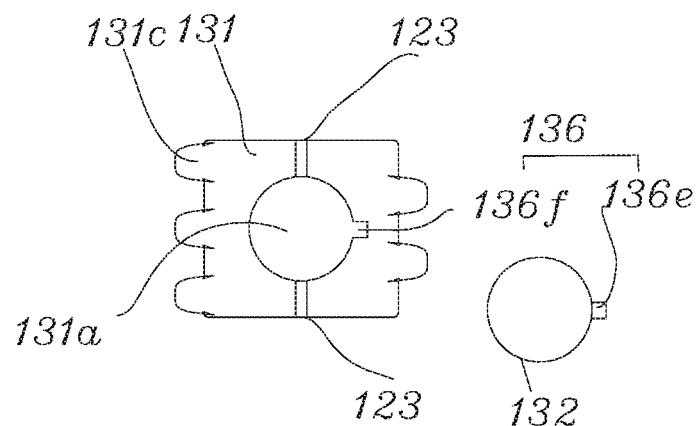
FIGS. 8 and 9 are schematic views of a stop mechanism according to a second embodiment in the present invention.
Figure 9:
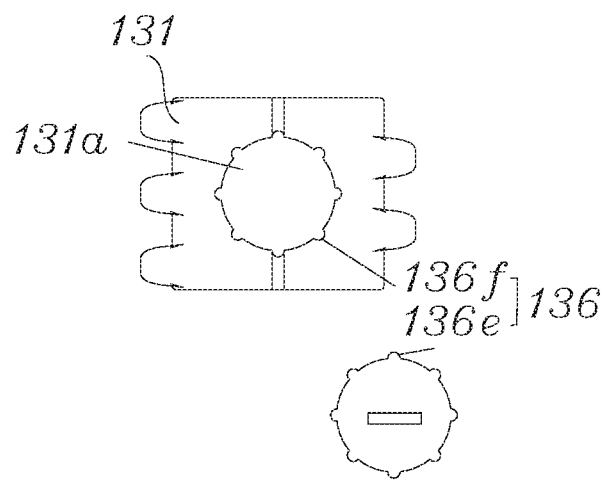

Except for the above embodiment, a second embodiment is shown in FIGS. 8 and 9. The stop mechanism 136 comprises a stop block 136e and a stop groove 136f. The stop block 136e is provided on the outer wall of the rotating member 132 or disposed on the inner wall of the receiving groove 131a, and the stop groove 136f is correspondingly formed on the inner wall of the receiving groove 131a or the outer wall of the rotating member 132. The length of the stop block 136e is greater than the width of the slot 134 formed between the receiving groove 131a and the rotating member 132. When the rotating member 132 is rotated to a predetermined angle, the stop block 136e is rotated into the stop groove 136f to lock them. The configurations of the stop block 136e and the stop groove 136f are not limited, and can include various configurations such as a protrusion or a rib. In this embodiment, the stop block 136e is a deformable rigid structure or made of a micro-elastic material, such as elastic sheets and plastic blocks, in order to achieve an effective locking effect without the influence on the rotation of the rotating member 132. In another embodiment, the stop block 136e can be connected with an elastic part, for example, a blind hole is formed in the wall surface of the rotating member 132 or the receiving groove 131a, a spring is disposed in the blind hole, and the stop block 136e is connected with the end of the spring. The stop block 136e is then pressed into the bind hole when the rotating member 132 is rotating, and when the stop block 136e rotates to the corresponding stop groove 136f, the stop block 136e is inserted into the stop groove 136f by the spring for stopping the rotation and to lock the position of the rotating member 132. The stop block 136e has a head portion in an arc shape which allows it to retract into the blind hole under the effect of an external force during rotation. One or more stop blocks 136e and one or more stop grooves 136f can be provided, and as shown in FIG. 9, multiple stop blocks 136e and multiple stop grooves 136f are provided. Specifically, multiple ribs are provided on the wall face of the receiving groove 131a or the rotating member 132 in the axial direction serving as the stop blocks 136e, and multiple strip-shaped stop grooves 136f are formed in the wall face of the corresponding rotating member 132 or receiving groove 131a in the axial direction.

Figure 10:
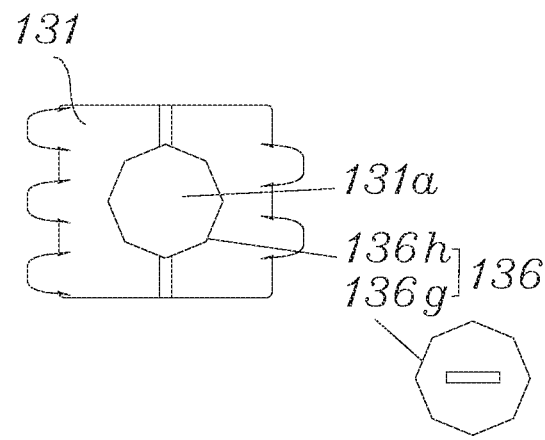
FIG. 10 is a schematic view of a stop mechanism according to a third embodiment in the present invention.

In addition, as shown in FIG. 10, the inner wall of the receiving groove 131a and the outer wall of the rotating member 132 have non-cylindrical configurations; preferably, the rotating member 132 and the receiving groove 131a are corresponding polygonal structures. At least one of the inner wall of the receiving groove 131a and the outer wall of the rotating member 132 is an elastic structure. The traction wire 122 is wound around the outer wall of the rotating member 132 after the rotating member 132 rotates in place. The inner wall of the receiving groove 131a and the outer wall of the rotating member 132 correspond to each other in shape to allow the rotating member 132 to stop its rotation after it is received in the receiving groove 131a. The non-cylindrical configurations can be polygonal structures, elliptic cylinder structures, star structures and so on. As shown in FIG. 10, the outer wall 136g of the rotating member 132 is polygonal-shaped which corresponds to the polygonal-shaped inner wall 136h of the receiving groove 131a.

Figure 11:
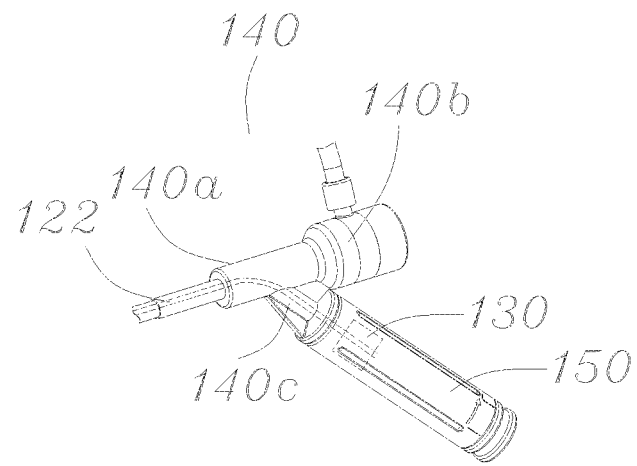
FIG. 11 is a schematic view of a handle portion according to the present invention.
Figure 12:
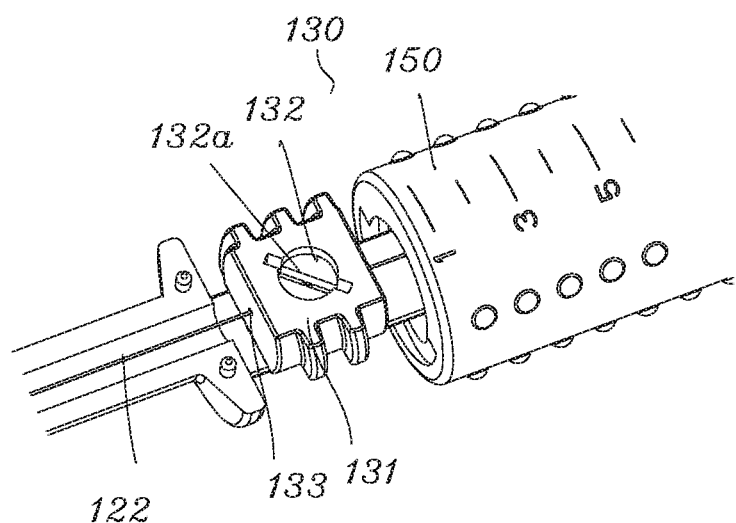
FIG. 12 is a schematic view of the retainer device without being assembled in a rotating drum according to the present invention.

A handle 140 of the adjustable curved medical catheter is shown in FIG. 11 and FIG. 12. The handle 140 in this embodiment is a Y-shaped handle. The supporting arm 140a is connected to the catheter, and the supporting arm 140b is connected to the conveying joint, respectively. The other supporting arm 140c of the Y-shaped handle is connected to the rotating drum 150 that houses the retainer device 130.

As shown in FIGS. 11 and 12, the rotating drum 150 is a component for adjusting the traction wire 122, and the rotating drum 150 surrounds the supporting arm 140c of the Y-shaped handle, and it can experience "limited rotation" on the supporting arm 140c. The term "limited rotation" refers to a rotation of the rotating drum 150 without being separated from the supporting arm 140c. This type of limited rotation can be realized by various limiting modes, for example, providing a plug, or a snap ring and the like, at the end of the supporting arm 140c to prevent the rotating drum 150 from separating from the supporting arm 140c. Threads are provided in the inner wall of the rotating drum 150, and a tooth groove is formed between two neighboring threads. The tooth groove couples with the rotating teeth 131c of the retainer device 130, and the rotating teeth 131c slide in the tooth groove. A self-locking mechanism is provided between the rotating drum 150 and the supporting arm 140c of the Y-shaped handle. When the rotating drum 150 rotates to the adjusted position, the self-locking mechanism locks the rotating drum 150, so that the rotating drum 150 no longer rotates relative to the supporting arm 140c, and the position of the retainer device 130 is locked and the traction wire 122 is correspondingly retained to pull the ring, all of which causes the front end of the catheter to be kept curved.

In order to prevent the retainer device 130 from rotating, a guide rail or a guide slot is formed on the supporting arm 140c, and the guide rail or the guide slot extends along the axial direction of the rotating drum 150. The retainer device 130 is coupled with the guide rail or the guide slot, and is driven to move back and forth along the guide rail or the guide slot by the rotating drum 150 that is rotating.

The supporting arms 140a and 140b of the Y-shaped handle are connected to the catheter and the conveying joint respectively. The connection structures thereof can be any known structure in the related art and will not be further described in detail.

Figure 13:
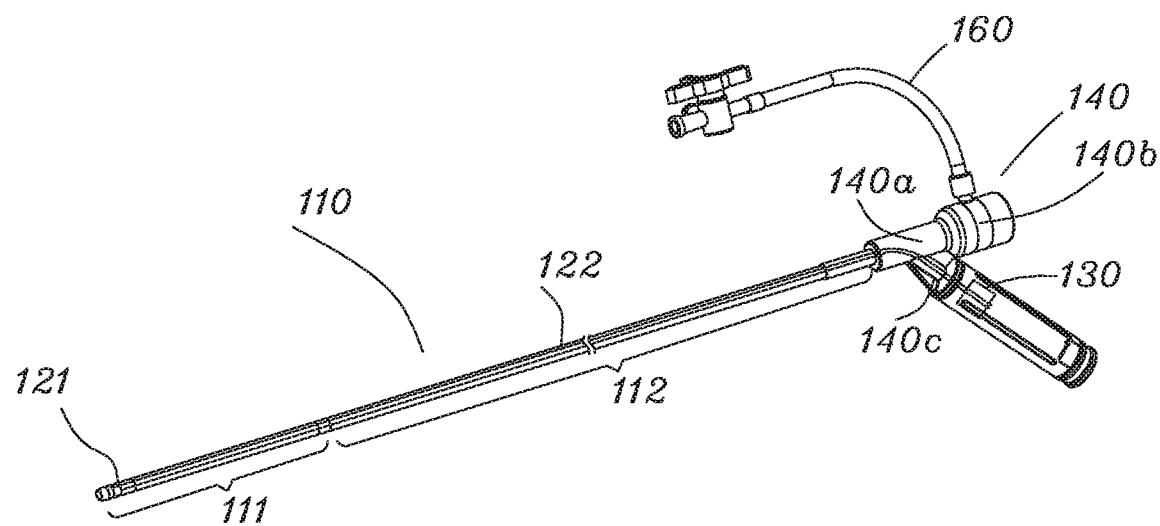
FIG. 13 is a schematic view of a catheter that is not curved according to the present invention.
Figure 14:
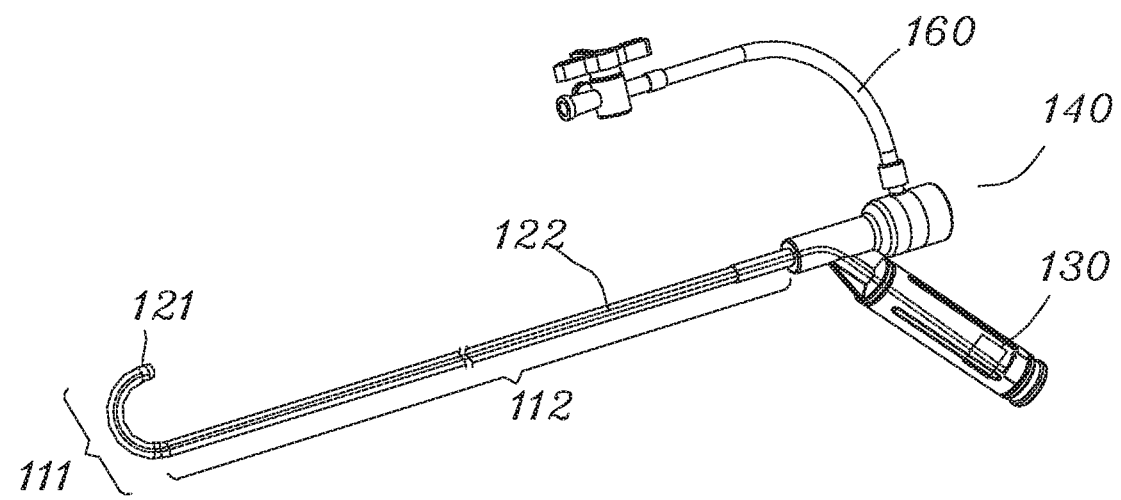
FIG. 14 is a schematic view of a catheter that is curved according to the present invention.
Figure 15:
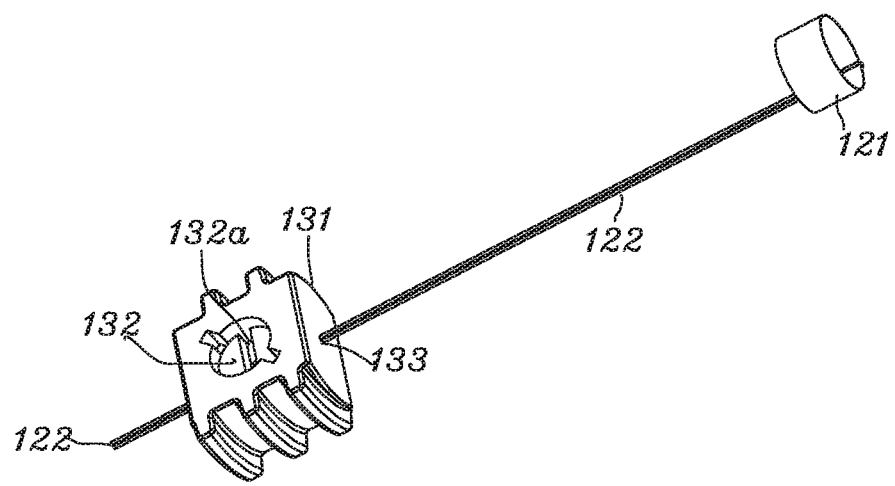
FIG. 15 is an assembled view of a traction wire assembled with the retainer device and a ring according to the present invention.

The adjustable curved medical catheter as shown in FIGS. 13 to 15 comprises a catheter 110, a handle 140 provided at the proximal end of the catheter 110, a ring 121 provided at the distal end of the catheter 110, and a traction wire 122 disposed in the traction cavity (not shown in the Figures) formed in the wall of the catheter 110. The distal end of the traction wire 122 is fixedly connected to the ring 121, and the proximal end of the traction wire 122 is connected to the handle 140. The handle 140 comprises a Y-shaped handle. Two of the three supporting arms 140a and 140b thereof are connected to the catheter 110 and the conveying joint 160 respectively, and the remaining supporting arm 140c of the Y-shaped handle is connected to the rotating drum 150 which houses the retainer device 130.

As shown in FIGS. 13 and 14, in the present invention, the catheter 110 assumes a straight tubular configuration when in a free state. The distal end of the catheter 110 is an elastic structural part 111 which can be curved and restored to its original shape within a certain range. The proximal end of the elastic structural part 111 is fixedly connected to a rigid structural part 112 which cannot be curved as desired. After the distal part of the elastic structural part 111 is adjusted to a smooth curve, damage caused by the movement in a human body lumen can be reduced. An inner delivery lumen is formed in the catheter 110 and a traction cavity is formed in the wall of the catheter 110 for receiving the traction wire 122. The ring 121 surrounds and is buried in the distal end of the elastic structural part 111, the distal end of the traction wire 122 is fixedly connected to the ring 121, and the proximal end of the traction wire 122 is connected to the handle 140. As shown in FIGS. 14 and 15, the traction wire 122 is adjusted by the handle 140, and the traction wire 122 pulls the ring 121 which causes the elastic structure part 111 of the catheter 110 to curve toward the traction wire 122. As shown in FIG. 13, when the handle 140 is adjusted in a reverse manner, the elastic structural part 111 is restored to a straight tubular configuration. The number and the position of the traction cavity and the traction wire are designed according to actual need for adjusting the curving direction of the elastic structural part 111 at the distal end of the catheter 110.

While the adjustable curved medical catheter is a medical apparatus which is widely applied to minimally invasive interventional diagnosis and therapy operation, there are many types of catheters. The assembling steps of the catheter can vary due to the various components thereof. However, based on the present invention, the adjustable curved medical catheter has the following common assembly steps: extending the proximal end of the traction wire through the guiding hole provided on the body of the retainer device, rotating the rotating member to drive the traction wire to rotate relative to the body and to be wound around the outer wall of the rotating member until the proximal end of the traction wire is received in the slot formed between the rotating member and the receiving groove of the body. Preferably, when the rotating member has a through hole extending through the guiding hole, the proximal end of the traction wire further extends through the through hole. This makes it easier for the traction wire to rotate relative to the body and be wound around the outer wall of the rotating member, and the engaging effect of the traction wire is improved.

Preferably, the assembling method further comprises the step of dropping fixing glue into the slot after the traction wire is engaged in the slot.

Other steps, for example, the assembly of the catheter and the traction mechanism, etc., associated with above steps are conventional technologies and will not be further described in detail.

In the assembly method described above, the fixing of the traction wire may be implemented simply by rotating the rotating member to drive the traction wire to engage with the slot and the rotating member. The retainer device can fix the traction wire without any exterior processing treatment (such as welding or pressing), so the process is simple and does not require additional devices or complex processing procedures, thereby reducing the personnel training and device maintenance costs.

The invention claimed is:

1. An adjustable curved medical device, comprising:
a catheter having a distal end, a proximal end;
a handle provided at the proximal end of the catheter;
a traction wire provided in the catheter having a length, and having a diameter, a distal end and a proximal end, with the distal end of the traction wire connected to the distal end of the catheter and the entire length of the traction wire positioned within the adjustable curved medical device and having its proximal end extending to the handle;
a retainer device provided in the handle and having a body and a rotating member, the body having a receiving groove for receiving the rotating member, the body also having an outer wall and an inner wall, and a guiding hole extending through the outer wall of the body to the receiving groove;
a slot formed between the rotating member and the inner wall of the body, wherein the slot has a diameter that is smaller than the diameter of the traction wire, and wherein the proximal end of the traction wire extends through the guiding hole and engages in the slot; and
a rotating drum in the handle, wherein, upon rotating the rotating drum, the retainer device slides in the axial direction of the rotating drum to drive the traction wire.

2. The device according to claim 1, wherein the rotating member has an outer wall that is provided with a rotating member groove, the rotating member groove having a depth, and the slot having a width, and wherein the sum of the depth of the rotating member groove and the width of the slot is smaller than the diameter of the traction wire, and the proximal end of the traction wire is sandwiched between the rotating member groove and the slot.

3. The device according to claim 1, wherein the rotating member has a through hole extending through the guiding hole, and the proximal end of the traction wire further extends through the through hole.

4. The device according to claim 1, wherein the rotating member has an outer wall, and wherein at least one of the outer wall of the rotating member and the inner wall of the body is elastically deformed under the winding and extrusion of the traction wire.

5. The device according to claim 1, wherein the rotating member and the body are respectively provided thereon with a separate stop mechanism cooperating with the rotating member and the body to fix the position of the rotating member after its rotation.

6. The device according to claim 5, wherein glue is applied to the slot to permanently fix the rotating member in the receiving groove.

7. The device according to claim 1, wherein the rotating member has an outer wall, and wherein at least one of the outer wall of the rotating member and the inner wall of the body is provided with an anti-slip member.

8. The device according to claim 1, wherein glue is applied to the slot to permanently fix the rotating member in the receiving groove.

9. The device according to claim 1, wherein the retainer device moves within the handle to drive the traction wire.

10. An adjustable curved medical device, comprising:
a catheter having a distal end, a proximal end;
a handle provided at the proximal end of the catheter;
a traction wire provided in the catheter having a length, and having a diameter, a distal end and a proximal end, with the distal end of the traction wire connected to the distal end of the catheter and the entire length of the traction wire positioned within the adjustable curved medical device and having its proximal end extending to the handle;
a retainer device provided in the handle and having a body and a rotating member, the body having a receiving groove for receiving the rotating member, the body also having an outer wall and an inner wall, and a guiding hole extending through the outer wall of the body to the receiving groove;
a slot formed between the rotating member and the inner wall of the body, wherein the slot has a diameter that is smaller than the diameter of the traction wire, and wherein the proximal end of the traction wire extends through the guiding hole and engages in the slot;
wherein the rotating member and the body are respectively provided thereon with a separate stop mechanism that comprises a stop groove that extends through a portion of the rotating member and a portion of the body to fix the position of the rotating member after its rotation.

11. The device according to claim 10, wherein the stop groove comprises a first stop groove formed in the rotating member and a second stop groove formed in the body, with the first and second stop grooves aligned with each other when the rotating member is rotated to a particular angle.

12. The device according to claim 10, wherein the stop mechanism further includes a stop block that is placed inside the stop groove.

13. An adjustable curved medical device, comprising:
a catheter having a distal end, and a proximal end;
a handle provided at the proximal end of the catheter;
a traction wire provided in the catheter and having a diameter, a distal end and a proximal end, with the distal end of the traction wire connected to the distal end of the catheter;
a retainer device provided in the handle and having a body and a rotating member, the body having a receiving groove for receiving the rotating member, the body also having an outer wall and an inner wall, and at least three guiding holes extending through the outer wall of the body to the receiving groove, with the proximal end of the traction wire extending through one pair of the guiding holes and turning back to extend through the remaining guiding holes; and
a slot formed between the rotating member and the inner wall of the body, wherein the slot has a diameter that is smaller than the diameter of the traction wire, and wherein the proximal end of the traction wire extends through one guiding hole of the at least three guiding holes and engages in the slot.

14. The device according to claim 13, wherein the rotating member has an outer wall that is provided with a rotating member groove, the rotating member groove having a depth, and the slot having a width, and wherein the sum of the depth of the rotating member groove and the width of the slot is slightly smaller than the diameter of the traction wire, and the proximal end of the traction wire is sandwiched between the rotating member groove and the slot.

15. The device according to claim 13, wherein the rotating member has a through hole extending through one guiding hole of the at least three guiding holes, and the proximal end of the traction wire further extends through the through hole.

16. The device according to claim 13, wherein the rotating member has an outer wall, and wherein at least one of the outer wall of the rotating member and the inner wall of the body is elastically deformed under the winding and extrusion of the traction wire.

17. The device according to claim 13, wherein the rotating member and the body are respectively provided thereon with a separate stop mechanism cooperating with the rotating member and the body to fix the position of the rotating member after its rotation.

18. The device according to claim 17, wherein the stop mechanism comprises a stop groove that extends through a portion of the rotating member and a portion of the body, and a stop block that is placed inside the stop groove.

19. The device according to claim 18, wherein the stop groove comprises a first stop groove formed in the rotating member and a second stop groove formed in the body, with the first and second stop grooves aligned with each other when the rotating member is rotated to a particular angle.

20. The device according to claim 13, wherein the rotating member has an outer wall, and wherein at least one of the outer wall of the rotating member and the inner wall of the body is provided with an anti-slip member.

\* \* \* \* \*